United States Patent
Kim et al.

(10) Patent No.: US 7,345,181 B2
(45) Date of Patent: Mar. 18, 2008

(54) PROCESS FOR PREPARING PROSTAGLANDIN DERIVATIVES AND STARTING MATERIALS FOR THE SAME

(75) Inventors: Yong-Hyun Kim, Seoul (KR); Yiu-Suk Lee, Seoul (KR)

(73) Assignee: Yonsung Fine Chemical Co., Ltd., Kyonggi-Do (KR)

( * ) Notice: Subject to any disclaimer, the term of this patent is extended or adjusted under 35 U.S.C. 154(b) by 562 days.

(21) Appl. No.: 10/528,256

(22) PCT Filed: Sep. 18, 2003

(86) PCT No.: PCT/KR03/01902

§ 371 (c)(1), (2), (4) Date: Mar. 17, 2005

(87) PCT Pub. No.: WO2004/026224

PCT Pub. Date: Apr. 1, 2004

(65) Prior Publication Data

US 2005/0272943 A1 Dec. 8, 2005

(30) Foreign Application Priority Data

Sep. 18, 2002 (KR) .................. 10-2002-0056836

(51) Int. Cl.
*C07D 307/77* (2006.01)

(52) U.S. Cl. .............. 549/458; 549/200; 549/429; 549/456

(58) Field of Classification Search ............... 549/200, 549/429, 456, 458
See application file for complete search history.

(56) References Cited

U.S. PATENT DOCUMENTS

| 5,202,447 | A | 4/1993 | Ohno et al. | |
| 5,233,059 | A | 8/1993 | Larock et al. | |
| 6,852,880 | B2 * | 2/2005 | Ham et al. | 562/465 |
| 6,989,458 | B2 * | 1/2006 | Ham et al. | 556/485 |

FOREIGN PATENT DOCUMENTS

| WO | WO-93/06095 | 4/1993 |
| WO | WO-2004/005274 | 1/2004 |

OTHER PUBLICATIONS

H. Wakita et al., "Heterocycles", vol. 48, No. 2, pp. 2559-2571 (1998).

* cited by examiner

*Primary Examiner*—Golam M. M. Shameem
(74) *Attorney, Agent, or Firm*—Peter F. Corless; Christine C. O'Day; Edwards Angell Palmer & Dodge LLP

(57) ABSTRACT

The present invention provides a process for preparing benzoprostacycline derivatives of formula (1), i.e. 5,6,7-trinor-4,8-inter-m-phenylene PGI2 derivatives, and vinyl tin compounds of formula (III) as starting materials for the same.

8 Claims, No Drawings

PROCESS FOR PREPARING PROSTAGLANDIN DERIVATIVES AND STARTING MATERIALS FOR THE SAME

TECHNICAL FIELD

The present invention relates to a process for preparing benzoprostacycline derivatives of the following formula:

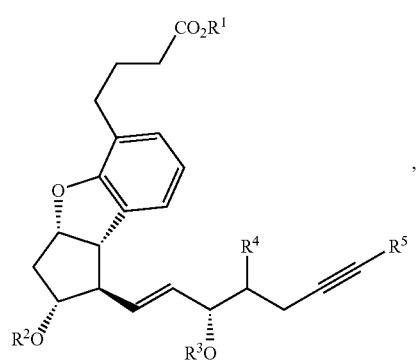

(I)

wherein $R^1$ represents a cation, H, or $C_{1-12}$alkyl, $R^2$ and $R^3$ each represent H or a hydroxy protective group, preferably, trimethylsilyl, triethylsilyl, t-butyldimethylsilyl, t-butyldiphenylsilyl, phenyldimethylsilyl, or tetrahydropyranyl, $R^4$ represents H or $C_{1-3}$alkyl, and $R^5$ represents H or $C_{1-6}$alkyl, i.e. 5,6,7-trinor-4,8-inter-m-phenylene $PGI_2$ derivatives. The present invention also relates to vinyl tin compounds of the following formula:

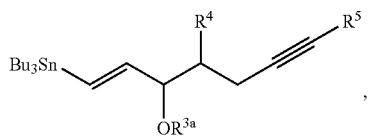

(III)

wherein $R^{3a}$ represents a hydroxy protective group, preferably, trimethylsilyl, triethylsilyl, t-butyldimethylsilyl, t-butyldiphenylsilyl, phenyldimethylsilyl, or tetrahydropyranyl, and $R^4$ and $R^5$ are each as defined above (Bu: Butyl), as starting materials for the above process.

BACKGROUND ART

Benzoprostacycline derivatives of formula (I) are known in the U.S. Pat. No. 5,202,447 and Tetrahedron Lett. 31, 4493 (1990), and their general synthetic method is depicted in the following reaction scheme:

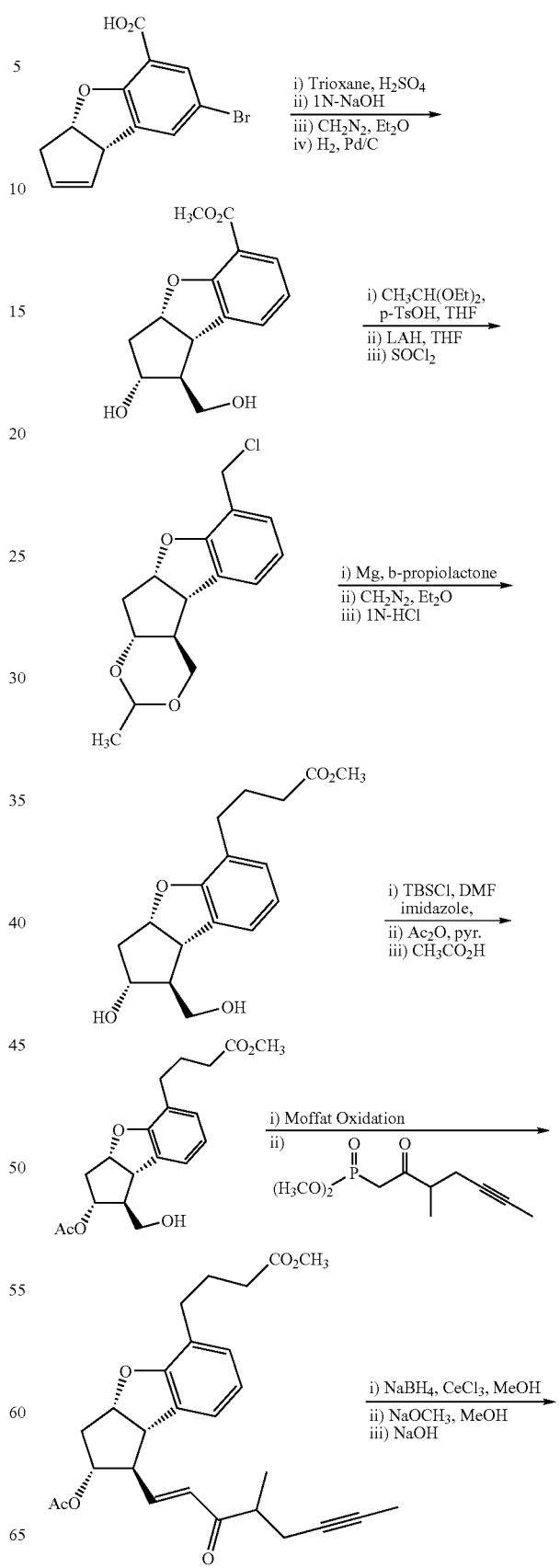

-continued

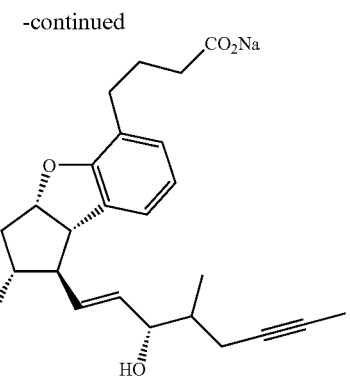

(Et: Ethyl, Ts: Tosyl, THF: Tetrahydrofuran, LAH: Lithium aluminum hydride, TBS: t-Butyldimethylsilyl, DMF: Dimethylformamide, pyr.: Pyridine, Ac: Acetyl, Me: Methyl)

Specifically, the above method comprises the steps of: i) forming a diol compound from a benzofuran ring via Prins reaction; ii) introducing a substituent to the benzene ring via Grignard reaction; iii) selectively protecting the diol, and then, introducing an ω-chain thereto via Wittig reaction; and iv) performing reduction, deacetylation and ester hydrolysis to the obtained compound under Luche condition. However, the method has drawbacks in that the diastereomeric mixture formed from reduction of $C_{15}$ ketone after ω-chain introduction has extremely low stereo-selectivity, i.e. the isomers ratio of 45:55, and a very low yield, i.e. 40%, of the desired isomer.

DISCLOSURE OF THE INVENTION

The present inventors have performed extensive studies to develop a process for preparing the compound of formula (I) which is not only economic but also efficient by solving the above-described problems of the known processes in the art. As a result, the present inventors invented novel compounds containing an ω-chain, and found that the above purpose could be attained by using the first step of performing 1,4-addition reaction of the ω-chain-containing compounds to α, β-unsaturated ketones to prepare the compound of formula (I). Thus, the present invention was completed.

One aspect of the present invention provides a process for preparing the compound of the following formula:

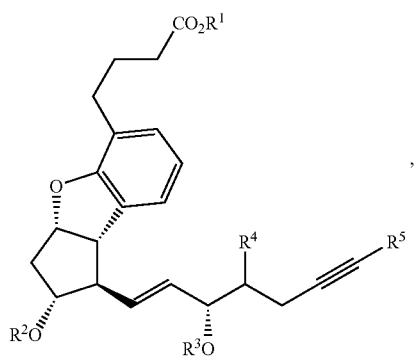

(I)

wherein $R^1$ represents a cation, H, or $C_{1-12}$alkyl, $R^2$ and $R^3$ each represent H or a hydroxy protective group, preferably, trimethylsilyl, triethylsilyl, t-butyldimethylsilyl, t-butyldiphenylsilyl, phenyldimethylsilyl or tetrahydropyranyl, $R^4$ represents H or $C_{1-3}$alkyl, and $R^5$ represents H or $C_{1-6}$alkyl, comprising the steps of:

(1) converting the compound of the following formula:

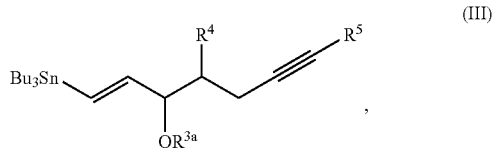

(III)

wherein $R^{3a}$ represents a hydroxy protective group, preferably, trimethylsilyl, triethylsilyl, t-butyldimethylsilyl, t-butyldiphenylsilyl, phenyldimethylsilyl, or tetrahydropyranyl, and $R^4$ and $R^5$ are each as defined above (Bu: Butyl), into its cuprate, and then, performing stereo-specific 1,4-addition reaction of the cuprate to an α,β-unsaturated ketone of the following formula:

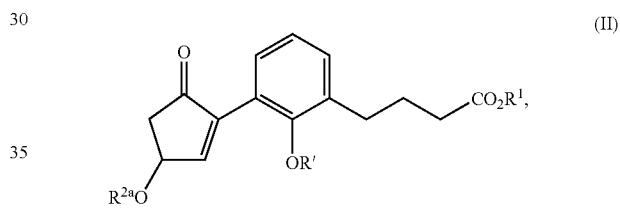

(II)

wherein $R^1$ is as defined above, $R^{2a}$ is as defined above for $R^{3a}$, and R' represents a hydroxy protective group, preferably, methyl, methoxymethyl, methoxyethyl, or a substituted methyl ether such as benzyloxymethyl, p-benzyloxymethyl, etc., to form a compound of the following formula (IV);

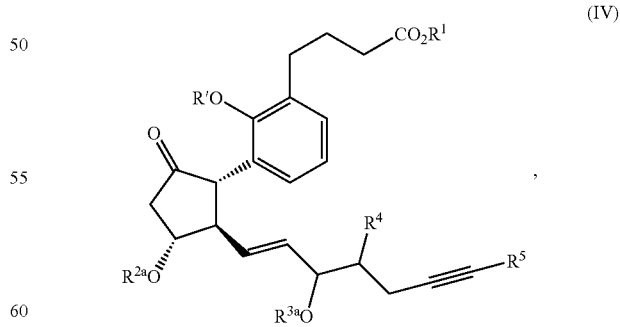

(IV)

wherein $R^1$, $R^{2a}$, $R^{3a}$, $R^4$, $R^5$ and R' are each as defined above;

(2) reducing the ketone of cyclopentanone in the compound of formula (IV) to form an α-alcohol compound of the following formula:

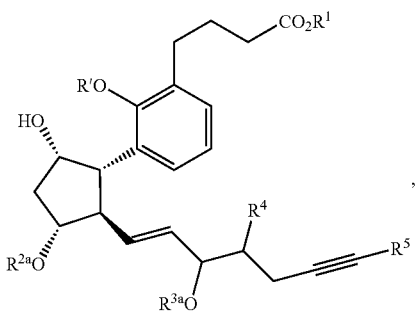

wherein $R^1$, $R^{2a}$, $R^{3a}$, $R^4$, $R^5$ and $R'$ are each as defined above;

(3) substituting the α-alcohol in the compound of formula (V) with a halide to form a β-halide compound of the following formula:

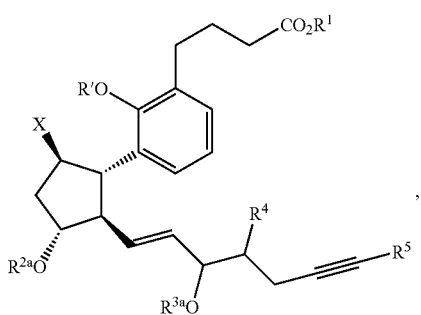

wherein $R^1$, $R^{2a}$, $R^{3a}$, $R^4$, $R^5$ and $R'$ are each as defined above, and X represents halo, preferably, chloro;

(4) deprotecting a hydroxy protective group of the compound of formula (VI) to form a compound of the following formula:

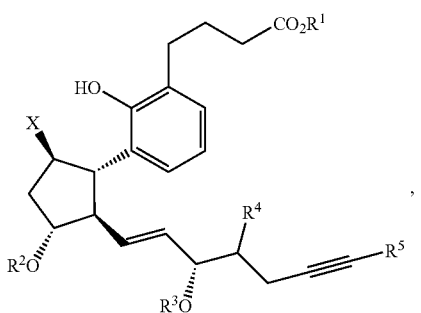

wherein $R^1$, $R^2$, $R^3$, $R^4$, $R^5$ and X are each as defined above;

(5) performing intramolecular cyclization to the compound of formula (VII) to form the compound of formula (I).

Another aspect of the present invention provides a compound of the following formula:

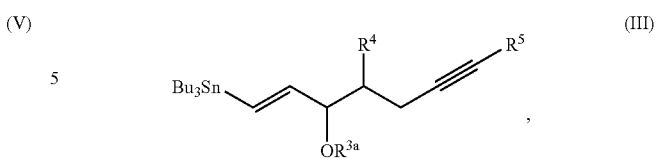

wherein $R^{3a}$, $R^4$ and $R^5$ are each as defined above.

Hereinafter, the present invention will be described in detail.

The compound of formula (III) used as a starting material for the preparation process of the present invention is novel, and the examples of its preparation processes include one comprising the step of reacting a compound of the following formula:

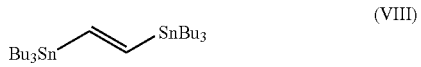

with a compound of the following formula:

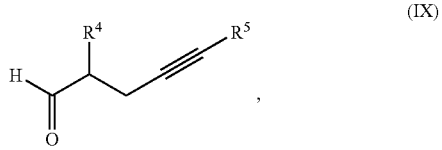

wherein $R^4$ and $R^5$ are each as defined above, and then protecting the resulting hydroxy group (process ⓐ); and one comprising the step of reacting the compound of formula (VIII) with a compound of the following formula:

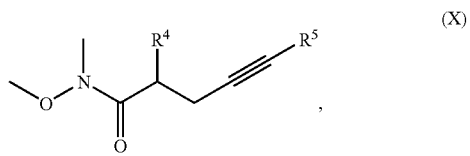

wherein $R^4$ and $R^5$ are each as defined above (process ⓑ).

a) Process ⓐ

The compound of formula (VIII) is dissolved in THF, and then, the resulting solution is cooled to −78° C. n-BuLi is slowly added thereto, and the mixture is stirred at the above temperature for 1 hour. Then, the compound of formula (IX) diluted in THF is added thereto, and the mixture is stirred for 5 minutes. Then, a hydroxy protective agent (e.g. TBSCl) is added thereto to obtain the compound of formula (III);

b) Process ⓑ

The compound of formula (VIII) is dissolved in THF, and then, the resulting solution is cooled to −78° C. n-BuLi is slowly added thereto, and the mixture is stirred at the above temperature for 1 hour. Then, the compound of formula (X) diluted in THF is added thereto, and the mixture is stirred for 5 minutes to stop the reaction with an aqueous solution of NH₄Cl. The reaction solution is extracted with diethyl ether, and the extract is concentrated. Thereto are added methanol and cerium chloride in the order. The ketone is reduced with sodium borohydride, and brine is added thereto. The mixture is extracted with hexane and the extract is concentrated. The concentrate is dissolved in DMF and a hydroxy protective agent (e.g. TBSCl) is added thereto to obtain the compound of formula (III).

The preparation process according to the present invention is depicted in the following reaction scheme:

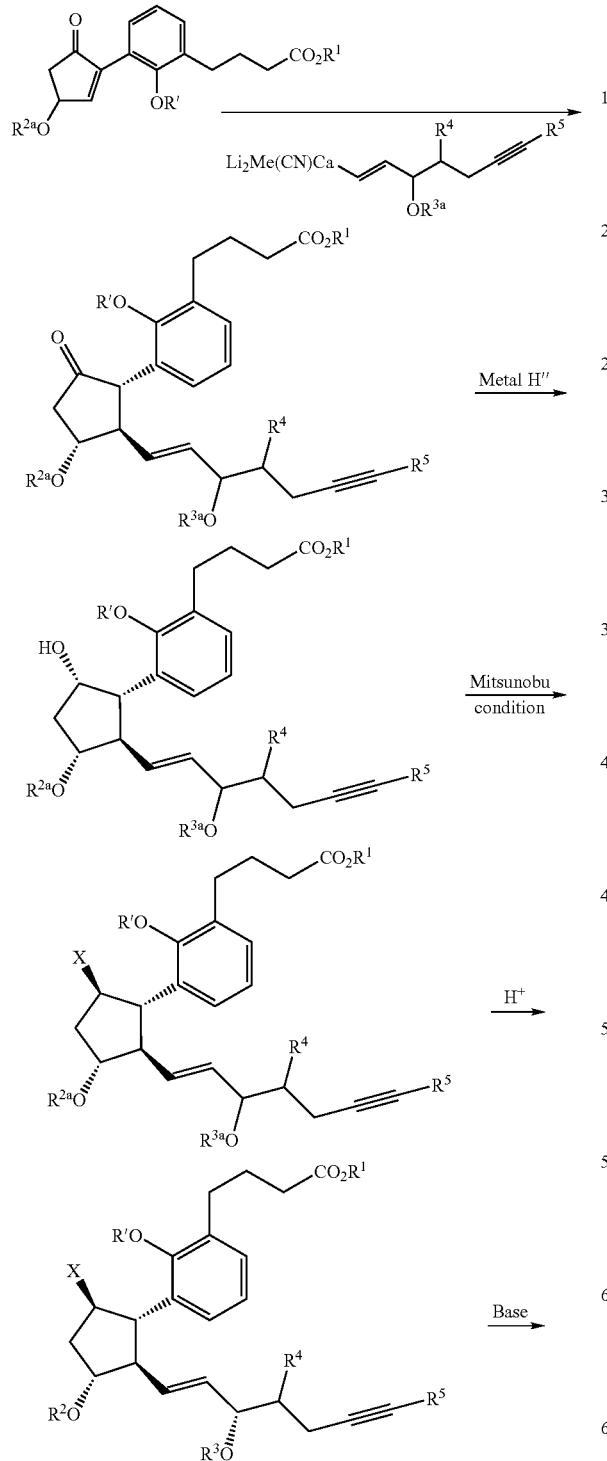

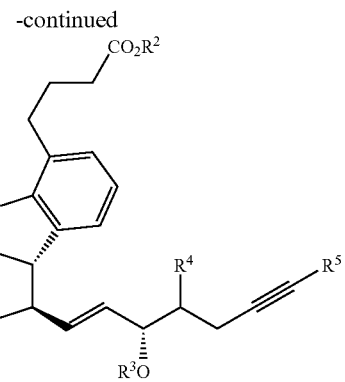

Each step of the preparation process according to the present invention will be explained below.

(1) First step: Preparation of the compound of formula (IV) from the compound of formula (II) and the compound of formula (III)

The compound of formula (IV) is prepared by conducting 1,4-addition reaction of a cuprate formed from a vinyl tin of formula (III) to an α,β-unsaturated ketone in the compound of formula (II). In this reaction, the cuprate is added to the opposite side of the alkoxy group (—$OR^{2a}$) substituted in the cyclopentanone ring due to steric hindrance from the alkoxy group, and so has trans-configuration with the alkoxy group. The added ω-chain causes another steric hindrance to the α-chain of the cyclopentanone to give the compound of formula (IV) with the stereochemistry of trans configuration between ω-chain and α-chain.

(2) Second step: Preparation of the compound of formula (V) by reduction of the compound of formula (IV)

The reduction of ketone present in the compound of formula (IV) may be carried out by using various kinds of metal hydride. The examples of metal hydride which may be used include sodium borohydride ($NaBH_4$), L-selectride, N-selectride, or K-selectride. L-selectride is preferable because a bulkier metal hydride has greater steric hindrance from the alkoxy group ($R^{2a}O$— or $R^{3a}O$—) substituted in the compound of formula (IV), and so the hydride attacks the cyclopentanone ring on the opposite side of the alkoxy group so that the desired α-alcohol can be selectively obtained. For this reaction, 1 to 3 equivalents of L-selectride is added to 1 equivalent of the compound of formula (IV) dissolved in a solvent at −78° C., and the mixture is stirred for 1 to 2 hours to stop the reaction with 30% $H_2O_2$. The reaction solution is stirred at 0° C. for 30 minutes, extracted with diethyl ether, and concentrated to stereo-selectively obtain the compound of formula (V). The compound is used in the subsequent reaction without any further purification. The examples of solvent which may be used include tetrahydrofuran, diethyl ether, and dichloromethane.

(3) Third step: Preparation of the compound of formula (VI) by halide substitution of the compound of formula (V)

The α-alcohol of formula (V) is substituted with a halide with various routes. In this process, the alcohol is converted into a leaving group, and then, the leaving group is converted into the β-halide via $S_N2$ reaction where the halide acts as a nucleophile. The examples of the leaving group include p-toluene sulfonate, methane sulfonate, trifluoromethane sulfonate, and the like, and the examples of the halide nucleophile include lithium halide, tetrabutylammonium halide, and the like. A method to directly convert the alcohol into the halide using trialkylphosphine and carbon tetrahalide may also be used. Preferable examples of the trialkylphosphine include tri-n-butylphosphine, triphenylphosphine and the like.

(4) Fourth step: Preparation of the compound of formula (VII) by deprotecting the compound of formula (VI)

The benzene ring present in the compound of formula (VI), and optionally, the hydroxy protective group(s) of cyclopentanone ring and/or of ω-chain can be deprotected under an acidic condition. The examples of acid which can be used include diluted hydrochloric acid, p-toluenesulfonic acid, pyridinium p-toluenesulfonic acid and the like, and the examples of solvent which can be used include methanol, ethanol, tetrahydrofuran, dichloromethane, acetone and mixed solvents thereof, etc.

(5) Fifth step: Preparation of the compound of formula (I) by intramolecular cyclization of the compound of formula (VII)

The compound of formula (I) can be prepared from the compound of formula (VII) via $S_N2$ reaction of a phenolic hydroxy group with a β-halide in the presence of various kinds of base. In this reaction, the examples of base include conventional base, for example, trialkylamine such as trimethylamine, triethylamine or diisopropylethylamine, and an inorganic base such as NaH, $K_2CO_3$, $Na_2CO_3$, $KHCO_3$ or $NaHCO_3$, particularly, $K_2CO_3$. The solvent may be polar or non-polar if it does not affect the reaction, but dimethylformamide (DMF), dimethylacetamide (DMA), tetrahydrofuran (THF), acetonitrile ($CH_3CN$), and so on are preferable, and $CH_3CN$ is particularly preferable. An appropriate reaction temperature is about 0 to 100° C.

BEST MODE FOR CARRYING OUT THE INVENTION

The present invention will be more specifically illustrated by the following examples. However, the following examples should not be construed as limiting the scope of the present invention in any way.

Preparation: Synthesis of t-butyldimethyl(2-methyl-1-(2-tributylstanyl-vinyl)4-hexynyloxy)silane Trans-bistributyltin ethylene (110 g, 181 mmol) was added to THF (500 ml), and the mixture was cooled to −78° C. BuLi (72 ml, 2.5 M in hexane, 181 mmol) was added thereto dropwise, and the mixture was stirred at the above temperature for 1 hour. Then, 2-methylhexyn-4-oic acid methoxymethylamide (25.5 g, 151 mmol) dissolved in THF (30 ml) was added thereto. The resulting mixture was stirred at the above temperature for 15 minutes, and then, a saturated aqueous solution of $NH_4Cl$ (100 ml) was added thereto. The reaction temperature was elevated to room temperature, and then, the reaction mixture was extracted with hexane. The obtained organic layer was dried over anhydrous magnesium sulfate, and then, filtered off, and concentrated under reduced pressure. The residue was dissolved in 1 l of methanol, and then, $CeCl_3$ (50 g, 136 mmol) was added thereto. The mixture was cooled to 0° C., and then, sodium borohydride (5.2 g, 136 mmol) was added thereto and the resulting mixture was stirred for 10 minutes. Brine of 500 ml was added thereto, and the mixture was extracted with hexane. The organic layer was dried over anhydrous magnesium sulfate, and then, filtered off, and concentrated under reduced pressure. Thereto were added DMF (500 ml), imidazole (27 g, 400 mmol), and TBSCl (30 g, 200 mmol) in the order, and the mixture was stirred for 12 hours. Upon completion of the reaction, the reaction solution was extracted with hexane, and the organic layer was dried over anhydrous magnesium sulfate, and then, filtered off, and concentrated under reduced pressure. The concentrate was subjected to column chromatography on a silica gel to obtain colorless transparent t-butyldimethyl(2-methyl-1-(2-tributylstanyl-vinyl)-4-hexynyloxy)silane (60 g, yield: 74%).

$^1$H NMR: 0.89 (m, 28H), 1.30-1.58 (m, 14H), 1.79 (t, 3H), 1.92-2.21 (m, 2H), 3.89 (dd, 1/2H), 4.06 (dd, 1/2H), 5.82-6.08 (m, 2H)

EXAMPLE 1

Synthesis of 4-(3-{3-(tert-butyl-dimethyl-silanyloxy)-2-[3-(tert-butyl-dimethyl-silanyloxy)-4-methyl-oct-1-en-6-ynyl]-5-oxo-cyclopentyl}-2-methoxymethoxy-phenyl)-butyric acid methyl ester

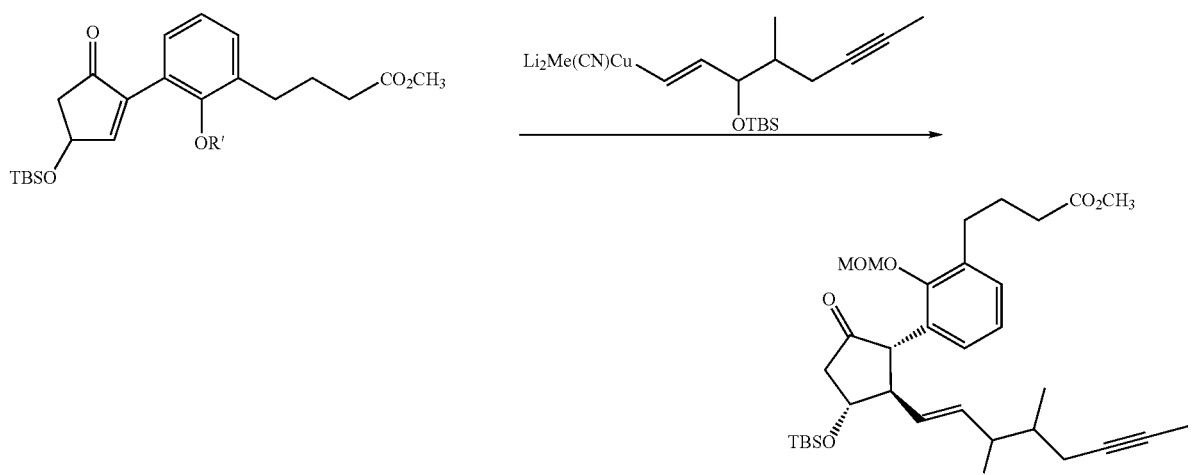

(MO: Methoxy)

CuCN (1.21 g, 13.5 mmol) was added to THF (15 ml), and the mixture was cooled to 0° C. MeLi (20.6 ml, 1.44 M in Et$_2$O, 29.7 mmol) was added thereto dropwise. t-Butyldimethyl(2-methyl-1-(2-tributylstanyl-vinyl)-4-hexynyloxy)silane (8.2 g, 15.2 mmol) was added thereto dropwise, and the mixture was stirred at room temperature for 2 hours. The reaction solution was cooled to −65° C., and thereto was added 4-{3-[3-(tert-butyl-dimethyl-silanyloxy)-5-oxo-cyclopent-1-enyl]-2-methoxymethoxy-phenyl}-butyric acid methyl ester (4.3 g, 9.6 mmol) dissolved in 15 ml of THF. The reaction temperature was elevated to −35° C. The mixture was stirred for 5 minutes, and then, added to a solution of NH$_4$Cl—NH$_3$ (9:1). The resulting mixture was stirred for 15 minutes, and extracted with diethyl ether. The organic layer was dried over anhydrous magnesium sulfate, and filtered off, and concentrated under reduced pressure. The concentrate was subjected to column chromatography on a silica gel (hexane:ethyl acetate=8:1) to obtain 4-(3-{3-(tert-butyl-dimethyl-silanyloxy)-2-[3-(tert-butyl-dimethyl-silanyloxy)-4-methyl-oct-1-en-6-ynyl]-5-oxo-cyclopentyl}-2-methoxymethoxy-phenyl)-butyric acid methyl ester (5.6 g, yield: 83%).

EXAMPLE 2

Synthesis of 4-(3-{3-(tert-butyl-dimethyl-silanyloxy)-2-[3-(tert-butyl-dimethyl-silanyloxy)-4-methyl-oct-1-en-6-ynyl]-5-hydroxy-cyclopentyl}-2-methoxymethoxy-phenyl)-butyric acid methyl ester

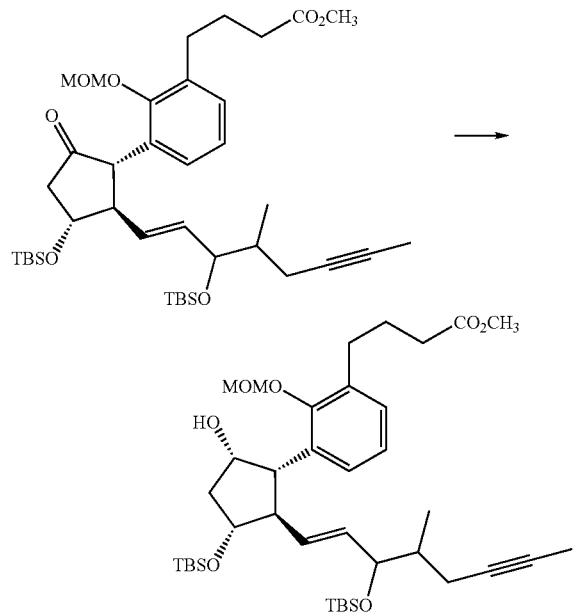

4-(3-{3-(tert-Butyl-dimethyl-silanyloxy)-2-[3-(tert-butyl-dimethyl-silanyloxy)-4-methyl-oct-1-en-6-ynyl]-5-oxo-cyclopentyl}-2-methoxymethoxy-phenyl)-butyric acid methyl ester of 2.6 g (3.67 mmol) was dissolved in THF (40 ml). The solution was cooled to −78° C., and then, L-selectride (1 M.THF solution, 7.35 mmol) was slowly added thereto dropwise. The mixture was stirred at the above temperature for 2 hours, and the reaction was stopped with hydrogen peroxide (30% aqueous solution, 16 mmol). The reaction solution was stirred at 0° C. for 30 minutes, and then, extracted with diethyl ether. The combined organic layer was washed with water and brine, and then, dried over magnesium sulfate, filtered off, and concentrated under reduced pressure. The concentrate was subjected to column chromatography on a silica gel (hexane:ethyl acetate=4:1) to obtain 4-(3-{3-(tert-butyl-dimethyl-silanyloxy)-2-[3-(tert-butyl-dimethyl-silanyloxy)-4-methyl-oct-1-en-6-ynyl]-5-hydroxy-cyclopentyl}-2-methoxymethoxy-phenyl)-butyric acid methyl ester (2.3 g, yield: 90%).

EXAMPLE 3

Synthesis of 4-(3-{3-(tert-butyl-dimethyl-silanyloxy)-2-[3-(tert-butyl-dimethyl-silanyloxy)-4-methyl-oct-1-en-6-ynyl]-5-chloro-cyclopentyl}-2-methoxymethoxy-phenyl)-butyric acid methyl ester

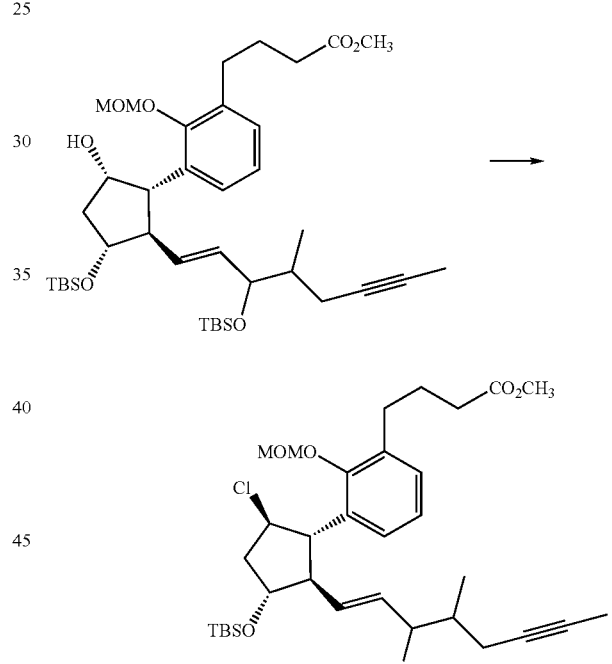

A mixture of 4-(3-{3-(tert-butyl-dimethyl-silanyloxy)-2-[3-(tert-butyl-dimethyl-silanyloxy)-4-methyl-oct-1-en-6-ynyl]-5-hydroxy-cyclopentyl}-2-methoxymethoxy-phenyl)-butyric acid methyl ester of 506 mg (0.72 mmol), triphenyl phosphine (350 mg, 1.34 mmol), CH$_3$CN (6 ml), pyridine (112 mg, 1.42 mmol), and CCl$_4$ (240 mg, 1.55 mmol) was stirred for 12 hours. The reaction solution was concentrated under reduced pressure, and then, subjected to column chromatography on a silica gel to obtain 4-(3-{3-(tert-butyl-dimethyl-silanyloxy)-2-[3-(tert-butyl-dimethyl-silanyloxy)-4-methyl-oct-1-en-6-ynyl]-5-chloro-cyclopentyl}-2-methoxymethoxy-phenyl)-butyric acid methyl ester (426 mg, yield: 82%).

EXAMPLE 4

Synthesis of 4-{3-[5-chloro-3-hydroxy-2-(3-(hydroxy-4-methyl-oct-1-en-6-ynyl]-cyclopentyl}-2-hydroxy-phenyl)-butyric acid methyl ester

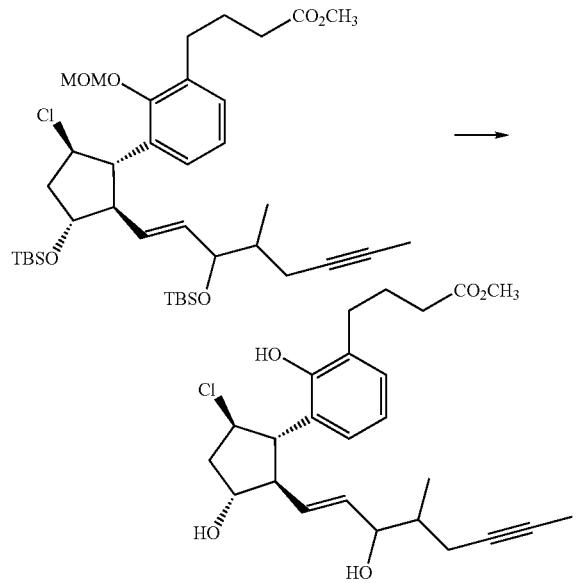

4-(3-{3-(tert-Butyl-dimethyl-silanyloxy)-2-[3-(tert-butyl-dimethyl-silanyloxy)-4-methyl-oct-1-en-6-ynyl]-5-chloro-cyclopentyl}-2-methoxymethoxy-phenyl)-butyric acid methyl ester of 939 mg (1.3 mmol) was dissolved in a mixed solution of methanol/dichloromethane (5:2) of 14 ml, and p-toluenesulfonic acid (895 mg, 5.2 mmol) was added thereto. The mixture was stirred at room temperature for 12 hours. Upon completion of the reaction, the reaction mixture was washed with an aqueous solution of sodium bicarbonate, and then, dried over anhydrous magnesium sulfate, filtered off, and concentrated under reduced pressure. The concentrate was subjected to column chromatography on a silica gel to obtain 4-{3-[5-chloro-3-hydroxy-2-(3-(hydroxy-4-methyl-oct-1-en-6-ynyl]-cyclopentyl}-2-hydroxy-phenyl)-butyric acid methyl ester (304 mg, yield: 52%).

EXAMPLE 5

Synthesis of 4-[2-hydroxy-3-(3-hydroxy-methyl-oct-1-en-6-ynyl)-2,3,3a,8a-tetrahydro-1H-8-oxa-cyclopenta[a]inden-7-yl]-butyric acid methyl ester

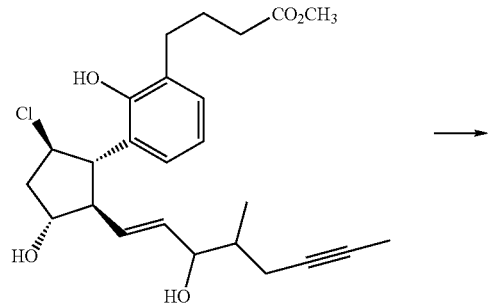

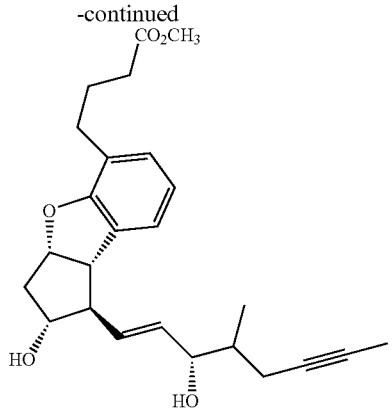

4-{3-[5-Chloro-3-hydroxy-2-(3-(hydroxy-4-methyl-oct-1-en-6-ynyl]-cyclopentyl}-2-hydroxy-phenyl)-butyric acid methyl ester of 1.12 g (2.5 mmol) was dissolved in acetonitrile of 10 ml. Then, potassium carbonate of 691 mg (5.0 mmol) was added thereto, and the mixture was stirred at room temperature for 4 hours. Upon completion of the reaction, the reaction solution was concentrated under reduced pressure, and thereto was added water of 10 ml. The resulting mixture was extracted three times with ethyl acetate of 10 ml. The combined organic layer was dried over anhydrous magnesium sulfate, and then, filtered off, and concentrated under reduced pressure. The concentrate was subjected to column chromatography on a silica gel (hexane: ethyl acetate=1:2) to obtain 4-[2-hydroxy-3-(3-hydroxy-4-methyl-oct-1-en-6-ynyl)-2,3,3a,8a-tetrahydro-1H-8-oxa-cyclopenta[a]inden-7-yl]-butyric acid methyl ester (980 mg, yield: 95%).

INDUSTRIAL APPLICABILITY

The process of the present invention can prevent yield decrease caused by the formation of isomers in ω-chain reduction, and by the separation of isomers in the final step. According to the present process, the desired product, the compound of formula (I), can be readily purified and obtained in a highly stereo-specific manner, and so prepared economically and efficiently.

What is claimed is:
1. A process for preparing a compound of the following formula:

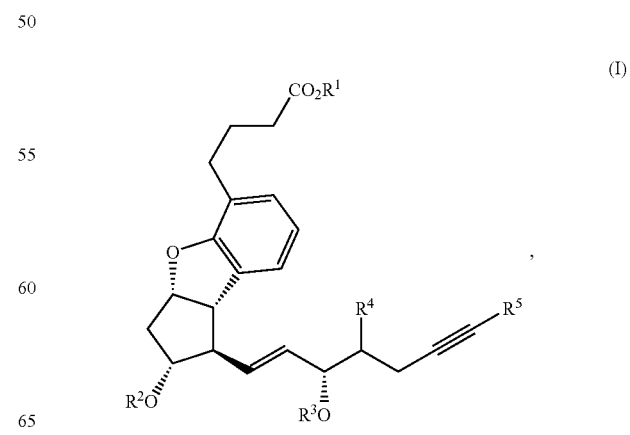

wherein $R^1$ represents a cation, H, or $C_{1-12}$alkyl,
$R^2$ and $R^3$ each represent H or a hydroxy protective group,
$R^4$ represents H or $C_{1-3}$alkyl, and
$R^5$ represents H or $C_{1-6}$alkyl, comprising the steps of:
(1) converting a compound of the following formula:

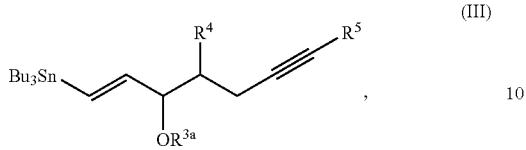
(III)

wherein $R^{3a}$ represents a hydroxy protective group, and $R^4$ and $R^5$ are each as defined above,
into its cuprate, and then, performing stereo-specific 1,4-addition reaction of the cuprate to an α, β-unsaturated ketone of the following formula:

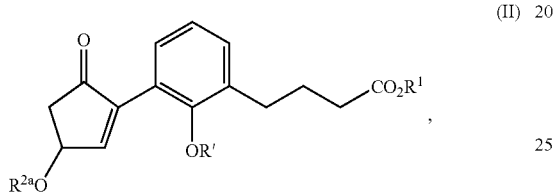
(II)

wherein $R^1$ is as defined above,
$R^{2a}$ represents a hydroxy protective group, and
R' represents a hydroxy protective group,
to form a compound of the following formula;

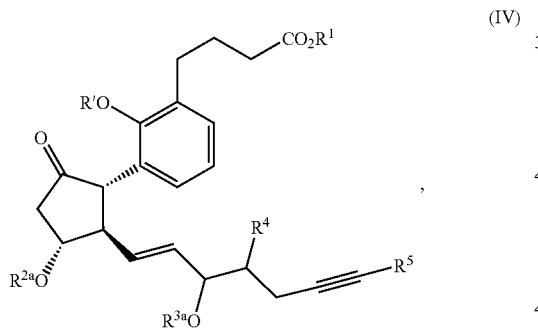
(IV)

wherein $R^1$, $R^{2a}$, $R^{3a}$, $R^4$, $R^5$ and R' are each as defined above;
(2) reducing a ketone of cyclopentanone in the compound of formula (IV) to form an α-alcohol compound of the following formula:

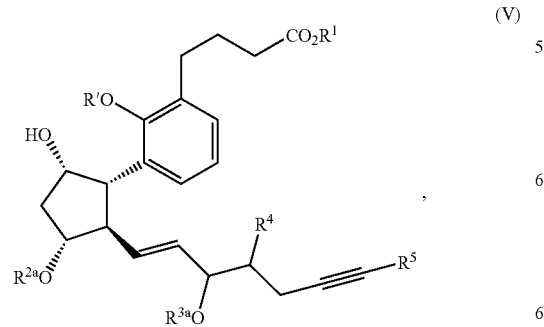
(V)

wherein $R^1$, $R^{2a}$, $R^{3a}$, $R^4$, $R^5$, and R' are each as defined above;
(3) substituting the α-alcohol of the compound of formula (V) with a halide to form a β-halide compound of the following formula:

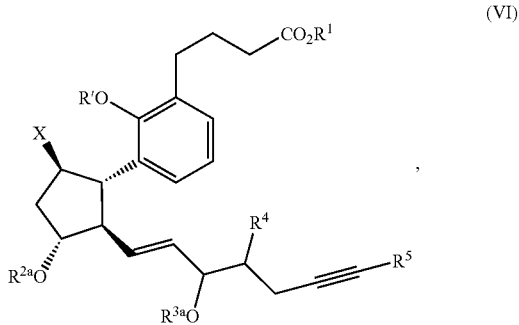
(VI)

wherein $R^1$, $R^{2a}$, $R^{3a}$, $R^4$, $R^5$ and R' are each as defined above, and
X represents halo;
(4) deprotecting a hydroxy protective group of the compound of formula (VI) to form a compound of the following formula:

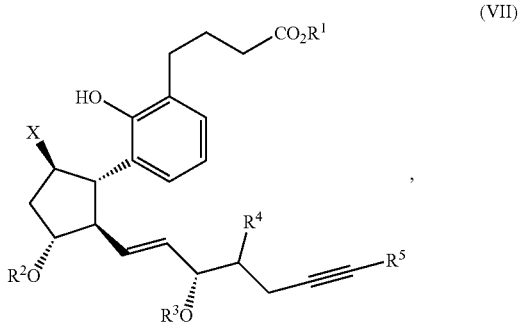
(VII)

wherein $R^1$, $R^2$, $R^3$, $R^4$, $R^5$, and X are each as defined above;
(5) performing intramolecular cyclization to the compound of formula (VII) to form the compound of formula (I).

2. The process of claim 1, wherein $R^2$, $R^3$, $R^{2a}$ and $R^{3a}$ each represent trimethylsilyl, triethylsilyl, t-butyldimethylsilyl, t-butyldiphenylsilyl, phenyldimethylsilyl, or tetrahydropyranyl, and R' represents methyl, methoxymethyl, methoxyethyl, benzyloxymethyl, or p-benzyloxymethyl.

3. The process of claim 1, wherein in step (2) the reduction is performed with using a metal hydride.

4. The process of claim 3, wherein the metal hydride is selected from the group consisting of sodium borohydride ($NaBH_4$), L-selectride, N-selectride and K-selectride.

5. The process of claim 1, wherein in step (3), i) the α-alcohol is converted into a leaving group, and then, the leaving group is converted into the β-halide via SN₂ reaction with the halide nucleophile, or ii) the α-alcohol is directly converted into the β-halide using trialkylphosphine and carbon tetrahalide.

6. The process of claim 1, wherein in step (4) the hydroxy protective group is deprotected under an acidic condition.

7. The process of claim 1, wherein in step (5) the cyclization reaction is performed in the presence of base.

8. A compound of the following formula:

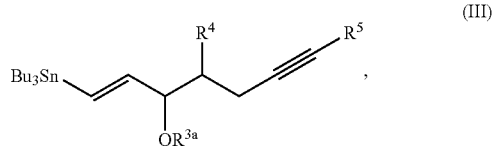

(III)

wherein $R^{3a}$, $R^4$ and $R^5$ are each as defined in claim 1.

* * * * *